United States Patent
Lai et al.

(10) Patent No.: US 9,572,555 B1
(45) Date of Patent: Feb. 21, 2017

(54) SPRAY OR DRIP TIPS HAVING MULTIPLE OUTLET CHANNELS

(71) Applicant: Ethicon, Inc., Somerville, NJ (US)

(72) Inventors: Gwan-Ywan Lai, Princeton Junction, NJ (US); Keith L. Jeffcoat, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 14/863,489

(22) Filed: Sep. 24, 2015

(51) Int. Cl.
  *B05B 7/00* (2006.01)
  *A61B 17/00* (2006.01)
  *B05B 7/04* (2006.01)

(52) U.S. Cl.
  CPC ....... *A61B 17/00491* (2013.01); *B05B 7/0408* (2013.01); *A61B 2017/00495* (2013.01); *A61B 2017/00522* (2013.01)

(58) Field of Classification Search
  CPC ............ B05B 7/00; B05B 7/04; B05B 7/0408; B05B 7/0884; B05B 7/0892; B05C 17/00; B05C 17/005; B05C 17/00543; B05C 17/00556; B05C 17/00559; B05C 17/0031; A61B 17/00491; A61B 2017/00495; A61B 2017/00522
  USPC ....... 239/541, 436–449, 570, 571, 574, 579, 239/310, 304, 321, 329, 418, 416.5, 427, 239/463, 466, 461, 399, 303, 398; 222/137, 145.1, 222/145.5, 145.6; 604/84, 604/82, 83, 191, 187
  See application file for complete search history.

(56) References Cited

U.S. PATENT DOCUMENTS

| | | | | |
|---|---|---|---|---|
| 2,584,827 A | * | 2/1952 | Bailey | B01F 5/0644 366/340 |
| 2,858,219 A | * | 10/1958 | Benson | A23L 7/135 425/308 |
| 3,032,239 A | * | 5/1962 | Whitley, Jr. | E01C 19/176 222/486 |
| 3,361,412 A | * | 1/1968 | Cole, III | B29B 7/325 138/42 |
| 3,682,446 A | * | 8/1972 | Eron | B01F 3/04446 366/266 |

(Continued)

FOREIGN PATENT DOCUMENTS

| | | |
|---|---|---|
| WO | WO 99/17833 | 4/1999 |
| WO | WO 2015/001638 | 1/2015 |
| WO | WO 2015/004709 | 1/2015 |

OTHER PUBLICATIONS

International Search Report re: PCT/US2016/051232 dated Nov. 3, 2016.
Written Opinion re: PCT/US2016/051232 dated Nov. 3, 2016.

*Primary Examiner* — Christopher Kim
*Assistant Examiner* — Viet Le
(74) *Attorney, Agent, or Firm* — David R. Crichton; Leo B. Kriksunov

(57) ABSTRACT

The present invention is directed to devices for mixing and expressing a multi-component sealant or hemostat or adhesive comprising at least two containers configured to contain and express two reactive components into separate lumens of a cannula. An elongated expression tip having a main channel that is open at a proximal end with the cannula slidably fits into the main channel. The tip contains a plurality of separate mixing chambers open at the distal end of the tip, wherein each of the mixing chambers is in fluid communication with the main channel via an individual connecting channel. Openings for each of the connecting channels are provided at different distances from the distal end. The tip is configured to slide on the cannula and advance distally when the main channel is pressurized due to an obstruction in at least one of the mixing chambers.

20 Claims, 10 Drawing Sheets

(56) References Cited

U.S. PATENT DOCUMENTS

| | | | | |
|---|---|---|---|---|
| 3,762,653 A | * | 10/1973 | Gibel | B05B 1/005 239/541 |
| 3,776,469 A | * | 12/1973 | Joannon | A61M 3/025 239/446 |
| 3,941,355 A | * | 3/1976 | Simpson | B01F 5/0656 222/145.2 |
| 4,027,857 A | * | 6/1977 | Cunningham | B01F 5/0645 366/340 |
| 4,040,420 A | * | 8/1977 | Speer | A61M 5/19 604/191 |
| 4,050,676 A | * | 9/1977 | Morishima | B01F 5/0644 366/339 |
| 4,072,271 A | * | 2/1978 | Voss | B05B 3/0472 239/541 |
| 4,195,780 A | * | 4/1980 | Inglis | B05B 1/005 165/908 |
| 4,204,775 A | * | 5/1980 | Speer | B01F 5/0647 366/336 |
| 4,316,673 A | * | 2/1982 | Speer | B01F 5/0609 366/337 |
| 4,461,454 A | * | 7/1984 | Vadnais | B05C 17/002 222/521 |
| 4,501,501 A | * | 2/1985 | Edwards | B01F 3/12 118/600 |
| 4,514,095 A | * | 4/1985 | Ehrfeld | B01F 5/0604 138/42 |
| 4,614,440 A | * | 9/1986 | King | B01F 5/0613 366/336 |
| 4,631,055 A | * | 12/1986 | Redl | A61B 17/00491 222/135 |
| 4,735,616 A | * | 4/1988 | Eibl | A61B 17/00491 604/191 |
| 4,846,405 A | * | 7/1989 | Zimmermann | A61B 17/00491 229/171 |
| 4,848,669 A | * | 7/1989 | George | B64D 13/00 239/539 |
| 4,900,572 A | * | 2/1990 | Repholz | A21C 11/163 425/131.1 |
| 4,966,468 A | * | 10/1990 | Bruning | B65D 81/3255 222/190 |
| 4,971,450 A | * | 11/1990 | Gerich | B01F 5/0644 366/340 |
| 5,094,793 A | * | 3/1992 | Schrenk | B01F 5/0644 264/173.15 |
| 5,116,315 A | * | 5/1992 | Capozzi | A61B 17/00491 222/137 |
| 5,297,697 A | * | 3/1994 | Boring | B05C 17/00516 137/68.23 |
| 5,299,866 A | * | 4/1994 | Osofsky | G01N 3/307 366/144 |
| 5,327,941 A | * | 7/1994 | Bitsakis | B01F 5/0682 138/42 |
| 5,437,784 A | * | 8/1995 | Meinecke | B01F 5/0646 209/170 |
| 5,443,183 A | * | 8/1995 | Jacobsen | B05C 17/00513 222/137 |
| 5,516,209 A | * | 5/1996 | Flint | B01F 5/0644 138/42 |
| 5,538,344 A | * | 7/1996 | Dybdahl | E21B 49/086 138/44 |
| 5,564,827 A | * | 10/1996 | Signer | B29C 47/362 366/336 |
| 5,582,596 A | * | 12/1996 | Fukunaga | A61B 17/00491 222/137 |
| 5,605,255 A | * | 2/1997 | Reidel | A61B 17/00491 222/137 |
| 5,605,541 A | * | 2/1997 | Holm | A61B 17/00491 604/68 |
| 5,609,300 A | * | 3/1997 | Conatser | B05B 1/3006 239/332 |
| 5,643,618 A | * | 7/1997 | Huberg | A21C 11/163 264/176.1 |
| 5,665,067 A | * | 9/1997 | Linder | A61B 17/00491 604/191 |
| 5,887,977 A | * | 3/1999 | Morikawa | B01F 5/0604 138/42 |
| 5,904,424 A | * | 5/1999 | Schwesinger | B01F 5/0604 138/42 |
| 5,909,959 A | * | 6/1999 | Gerich | B01F 5/0615 222/459 |
| 5,937,906 A | * | 8/1999 | Kozyuk | B01F 5/0661 138/37 |
| 5,989,215 A | * | 11/1999 | Delmotte | A61L 15/32 604/191 |
| 6,000,637 A | * | 12/1999 | Duncan | B05B 1/3006 137/489.5 |
| 6,021,961 A | * | 2/2000 | Brown | B29B 7/7438 239/398 |
| 6,063,055 A | * | 5/2000 | Epstein | A61B 17/00491 604/191 |
| 6,126,091 A | * | 10/2000 | Heitzman | B05B 1/1636 239/380 |
| 6,132,079 A | * | 10/2000 | King | B01F 5/0644 366/175.2 |
| 6,145,544 A | * | 11/2000 | Dutertre | F16L 55/02718 138/39 |
| 6,176,437 B1 | * | 1/2001 | Pedersen | B05B 1/005 137/624.14 |
| 6,186,179 B1 | * | 2/2001 | Hill | F15D 1/0005 138/39 |
| 6,217,208 B1 | * | 4/2001 | Schuchardt | B01F 5/061 366/147 |
| 6,234,365 B1 | * | 5/2001 | Bougamont | A61M 11/06 222/189.06 |
| 6,321,998 B1 | * | 11/2001 | Schubert | B01F 5/0256 239/430 |
| 6,328,229 B1 | * | 12/2001 | Duronio | B01F 5/0057 222/145.5 |
| 6,383,422 B1 | * | 5/2002 | Hoffschmidt | B01D 39/2093 210/510.1 |
| 6,398,761 B1 | * | 6/2002 | Bills | A61C 5/062 222/145.5 |
| 6,454,739 B1 | * | 9/2002 | Chang | A61B 17/00491 239/399 |
| 6,458,095 B1 | * | 10/2002 | Wirt | A61B 17/00491 222/137 |
| 6,461,361 B1 | * | 10/2002 | Epstein | A61B 17/00491 222/145.2 |
| 6,509,049 B1 | * | 1/2003 | Parsons | A21C 11/163 366/173.2 |
| 6,568,845 B1 | * | 5/2003 | Harada | B01F 5/0603 366/340 |
| 6,585,407 B2 | * | 7/2003 | Koch | B01F 5/0617 366/336 |
| 6,585,696 B2 | * | 7/2003 | Petersen | A61B 17/00491 222/391 |
| 6,613,020 B1 | * | 9/2003 | Holm | A61B 17/00491 222/137 |
| 6,620,125 B1 | * | 9/2003 | Redl | A61B 17/00491 222/145.6 |
| 6,629,774 B1 | * | 10/2003 | Gruendeman | B05C 17/002 222/145.6 |
| 6,631,737 B1 | * | 10/2003 | Kipping | G05D 7/012 138/43 |
| 6,719,729 B2 | * | 4/2004 | Sogaro | A61M 5/19 222/145.5 |
| 6,764,467 B1 | * | 7/2004 | Roby | A61B 17/00491 222/129 |
| 6,773,414 B2 | * | 8/2004 | Ljungquist | A61B 17/00491 604/70 |
| 6,802,640 B2 | * | 10/2004 | Schubert | B01F 5/0644 366/181.6 |
| 6,802,822 B1 | * | 10/2004 | Dodge | A61B 17/00491 604/82 |
| 6,921,380 B1 | * | 7/2005 | Epstein | A61M 37/00 222/137 |
| 6,921,381 B2 | * | 7/2005 | Spero | A61B 17/00491 604/82 |

(56) References Cited

U.S. PATENT DOCUMENTS

| | | | | |
|---|---|---|---|---|
| 7,018,357 B2* | 3/2006 | Emmons | A61B 17/00491 | 222/134 |
| 7,134,613 B2* | 11/2006 | Kah, III | B05B 3/045 | 239/237 |
| 7,135,027 B2* | 11/2006 | Delmotte | A61B 17/8816 | 606/92 |
| 7,198,400 B2* | 4/2007 | Unterlander | B01F 5/0645 | 366/336 |
| 7,220,048 B2* | 5/2007 | Kohlgruber | B01F 3/10 | 165/172 |
| 7,240,483 B2* | 7/2007 | Cizeron | F01N 3/023 | 422/182 |
| 7,252,847 B2* | 8/2007 | Keller | B29C 47/0028 | 426/249 |
| 7,284,902 B2* | 10/2007 | Hosozawa | B01F 5/0641 | 366/336 |
| 7,384,007 B2* | 6/2008 | Ho | B05B 1/1663 | 239/553 |
| 7,464,885 B1* | 12/2008 | Chang | B05B 1/3013 | 239/463 |
| 7,520,661 B1* | 4/2009 | Lawson | B01F 5/0604 | 138/42 |
| 7,537,174 B2* | 5/2009 | Redl | A61B 17/00491 | 222/137 |
| 7,552,741 B2* | 6/2009 | Yamada | B01F 5/045 | 137/3 |
| 7,559,296 B2* | 7/2009 | Perotto | F01P 3/08 | 123/41.35 |
| 7,575,131 B2* | 8/2009 | Feinberg | A61B 17/00491 | 222/1 |
| 7,594,616 B2* | 9/2009 | Hupp | F16K 23/00 | 141/311 A |
| 7,635,343 B2* | 12/2009 | McIntosh | A61B 17/00491 | 604/82 |
| 7,681,807 B2* | 3/2010 | Gregory | B05B 1/3006 | 239/203 |
| 7,744,019 B2* | 6/2010 | Merchant | B01F 5/0615 | 239/411 |
| 7,887,698 B2* | 2/2011 | Wood | A01K 63/042 | 210/199 |
| 7,891,583 B2* | 2/2011 | Sayers | B05B 11/3032 | 222/207 |
| 7,963,937 B2* | 6/2011 | Pauser | A61C 9/0026 | 222/129 |
| 8,033,483 B2* | 10/2011 | Fortier | A61B 17/00491 | 222/137 |
| 8,132,961 B1* | 3/2012 | England | B01F 5/0428 | 366/340 |
| 8,241,410 B1* | 8/2012 | Pease | B01D 47/10 | 261/DIG. 54 |
| 8,323,227 B2* | 12/2012 | Hamatake | A61M 1/3653 | 604/264 |
| 8,408,228 B1* | 4/2013 | Jimenez | F16K 43/006 | 137/498 |
| 8,534,575 B2* | 9/2013 | Brem | A61B 17/00491 | 222/137 |
| 8,567,700 B2* | 10/2013 | Miedzius | B05B 1/3086 | 239/457 |
| 8,616,468 B2* | 12/2013 | Hull | A61B 17/00491 | 239/400 |
| 8,622,974 B2* | 1/2014 | Alvey | A61J 1/2093 | 604/181 |
| 8,753,670 B2* | 6/2014 | Delmotte | A61L 15/44 | 424/443 |
| 8,870,028 B2* | 10/2014 | Kane | B65D 81/3255 | 222/135 |
| 9,010,994 B2* | 4/2015 | McQueen | B01F 5/0618 | 366/337 |
| 2002/0138038 A1* | 9/2002 | Ljungquist | A61B 17/00491 | 604/82 |
| 2004/0130967 A1* | 7/2004 | Wolf | B01F 5/0603 | 366/340 |
| 2005/0252997 A1* | 11/2005 | Gluck | F01M 1/16 | 239/541 |
| 2007/0160890 A1* | 7/2007 | Fischer | B01F 5/0421 | 429/414 |
| 2007/0246567 A1* | 10/2007 | Roberts | B05B 1/3006 | 239/200 |
| 2008/0097389 A1* | 4/2008 | Wilson | A61M 1/0281 | 604/518 |
| 2008/0211119 A1* | 9/2008 | Nieminen | B01F 3/0446 | 261/76 |
| 2009/0038701 A1* | 2/2009 | Delmotte | B01F 5/0682 | 137/896 |
| 2009/0076459 A1* | 3/2009 | Goldberg | A61B 17/00491 | 604/191 |
| 2009/0124986 A1* | 5/2009 | Hayakawa | B01F 5/0262 | 604/290 |
| 2009/0266918 A1* | 10/2009 | Fortier | A61B 17/00491 | 239/398 |
| 2009/0314010 A1* | 12/2009 | Flamant | B01F 15/063 | 62/64 |
| 2010/0065660 A1* | 3/2010 | Hull | A61B 17/00491 | 239/428 |
| 2010/0082013 A1* | 4/2010 | Braga | A61M 5/31596 | 604/518 |
| 2010/0094208 A1* | 4/2010 | Branchetti | A61B 17/00491 | 604/82 |
| 2010/0096481 A1* | 4/2010 | Hull | A61B 17/00491 | 239/600 |
| 2010/0121268 A1* | 5/2010 | Keller | A61B 17/00491 | 604/82 |
| 2010/0204679 A1* | 8/2010 | Denenburg | A61J 1/2096 | 604/518 |
| 2010/0206905 A1* | 8/2010 | Horner | A61C 5/064 | 222/137 |
| 2010/0274279 A1* | 10/2010 | Delmotte | A61B 17/00491 | 606/213 |
| 2010/0281869 A1* | 11/2010 | Hadley | F23R 3/12 | 60/734 |
| 2010/0318063 A1* | 12/2010 | Soll | A61M 5/19 | 604/518 |
| 2011/0021982 A1* | 1/2011 | Keller | A61B 17/00491 | 604/82 |
| 2011/0092899 A1* | 4/2011 | Ohri | A61B 17/00491 | 604/82 |
| 2011/0106071 A1* | 5/2011 | Bosel | A61B 18/06 | 606/28 |
| 2011/0118664 A1* | 5/2011 | Greter | A61B 17/00491 | 604/82 |
| 2011/0147491 A1* | 6/2011 | Pope | B05B 7/045 | 239/398 |
| 2011/0158852 A1* | 6/2011 | Castro | B01F 5/0641 | 422/69 |
| 2011/0197587 A1* | 8/2011 | Zuo | F23D 14/02 | 60/740 |
| 2011/0210184 A1* | 9/2011 | Maas | B05B 7/0433 | 239/8 |
| 2011/0319930 A1* | 12/2011 | Roush | A61B 17/00491 | 606/213 |
| 2012/0101478 A1* | 4/2012 | Stroumpoulis | A61M 5/19 | 604/518 |
| 2012/0158048 A1* | 6/2012 | Roush | A61B 17/00491 | 606/214 |
| 2012/0228329 A1* | 9/2012 | Staub | B65D 81/325 | 222/137 |
| 2012/0241475 A1* | 9/2012 | Dennis | B05B 11/3009 | 222/137 |
| 2012/0263672 A1* | 10/2012 | Artzi | A61L 24/08 | 424/78.17 |
| 2012/0279988 A1* | 11/2012 | Hiemer | A61C 9/0026 | 222/82 |
| 2012/0298780 A1* | 11/2012 | Frick | F16K 15/08 | 239/571 |
| 2012/0330228 A1* | 12/2012 | Day | A61M 5/14244 | 604/82 |
| 2013/0021868 A1* | 1/2013 | Doolin | B01F 5/0415 | 366/154.1 |

(56) References Cited

U.S. PATENT DOCUMENTS

| | | | |
|---|---|---|---|
| 2013/0021871 A1* | 1/2013 | Strahmann | B01F 5/0682 366/340 |
| 2013/0060232 A1* | 3/2013 | Adlon | A61M 5/2066 604/506 |
| 2013/0065973 A1* | 3/2013 | Hirschberg | B01F 5/0691 516/9 |
| 2013/0082071 A1* | 4/2013 | Ritzenhoff | B05B 11/3083 222/137 |
| 2013/0105601 A1* | 5/2013 | Henry | A62C 5/022 239/407 |
| 2013/0116617 A1* | 5/2013 | Martin | A61M 5/3294 604/82 |
| 2013/0126557 A1* | 5/2013 | Turner | B01F 5/0615 222/137 |
| 2013/0277390 A1* | 10/2013 | Buck | B05C 17/00553 222/80 |
| 2013/0317423 A1* | 11/2013 | Kane | B65D 81/3255 604/82 |
| 2014/0107620 A1* | 4/2014 | Fech | A61M 25/0067 604/518 |
| 2014/0117116 A1* | 5/2014 | Masson | B01F 13/0027 239/310 |
| 2014/0155819 A1* | 6/2014 | Amirouche | A61M 5/1723 604/82 |
| 2014/0197204 A1* | 7/2014 | Bublewitz | B05C 17/00513 222/145.5 |
| 2014/0203042 A1* | 7/2014 | Tsai | B65D 83/0033 222/80 |
| 2014/0241960 A1* | 8/2014 | Mochizuki | B01F 5/12 422/633 |
| 2014/0246457 A1* | 9/2014 | Miyano | B05C 17/00553 222/137 |
| 2014/0276384 A1* | 9/2014 | Schwab | A61K 35/35 604/82 |

* cited by examiner

SPRAY OR DRIP TIPS HAVING MULTIPLE OUTLET CHANNELS

FIELD OF THE INVENTION

The present disclosure relates to drip or spray tip assemblies for use with devices that mix and apply two or more components. More particularly, the present disclosure relates to a tip assembly, wherein the tip automatically, semi-automatically, or manually changes to a fresh mixing chamber and it thus is capable of redirecting flow when clogging occurs.

BACKGROUND

Drip or spray devices for dispensing two or more synthetic or biologics based sealant components are known. In the medical device field, such devices are typically used for applying bioadhesives, polymers and other synthetic materials used as wound closures. Because of the reactant nature of the biocomponents used to form the bioadhesive blends, mixing of the components does not occur until the solution is ready to be applied. Mixing of the components too soon before application may result in premature hardening of the mixture, thereby making application of the solution impossible. Thus, in known spray or drip devices, the two or more components are maintained separately until just prior to application. The drip devices include one or more mixing means for mixing the two or more components prior to application. The mixing means may be passive, i.e., spiral configuration in the tubing, or instead may be active, i.e., mixing blade or impeller, with active mixing requiring more complex devices design. Once mixed, the solution may be applied through a needle-like output or may instead be ejected through a spray assembly. Thorough mixing of the two or more components prior to application is important to ensure that the solution will perform as intended.

An exemplary device is taught in U.S. Pat. No. 5,116,315, entitled "Biological Syringe System", which discloses a system for delivery two fluids in a mixed composition, comprising a manifold and a discharge assembly. The discharge assembly mixes fluids in a mixing space and then atomizes the mixed fluids in a spray delivered from the assembly. Similarly, the device shown in U.S. Pat. No. 5,605,255, entitled, "Apparatus for Spraying a mixture of Two Components", is an apparatus for spraying a liquid mixture having two syringes, a connecting piece, a premixing chamber, and a reduced volume section downstream from premixing chamber, and an exit aperture for spraying the mixture. The reduced volume section terminates in a homogenization region. U.S. Pat. No. 6,063,055, entitled "Turbulence Mixing Head for a Tissue Sealant Applicator and Spray Head for Same", illustrates a device in which the mixing is performed in a mixing head.

Intermittent use of a biologics spray device, as may be required during a procedure, tends to clog the outlet of the applicator tip. As a result, most applicator assemblies are provided with a number of replacement tips for use when clogging of the tip occurs. Replacing clogged applicator tips interrupts the flow of a procedure, is time consuming and is an added expense. The device in published U.S. Publication 2010/0096481, "Self-Cleaning Spray Tip", is described as having the distal end of spray cap assembly with an outlet that changes its configuration—at rest and at a second condition (e.g. during expression). The distal end is described as comprised of a material that permits flexion and expansion. The first and second reactive components are introduced into swirl chambers before mixing and are atomized as ejected through the outlet in a cone-shaped spray U.S. Pat. No. 5,605,541 "Fibrin sealant applicator" discloses a device for applying a fibrin sealant comprising two components which will form said sealant when combined, which device comprises commonly actuable reservoirs for each of said components and a source of gas, wherein each of said reservoirs and said gas in separate fluid communication via a discrete channel to a spray head, said spray head having a first aperture located centrally in an exit end of said spray head through which said gas is discharged, said spray head having a first annular aperture in the exit end of said spray head within first annular aperture is concentric with said first aperture and through which one of said fibrin-sealant-forming components is discharged, and a second annular aperture in the exit end of said spray head being concentric with said first aperture and concentric with, and having a radius larger than said first annular aperture through which the second of said fibrin-sealant-forming components is discharged wherein all of said apertures are in a common plane.

U.S. Pat. No. 6,773,414 "Device and method for dispensing at least two mutually reactive components" discloses a device for dispensing at least two mutually reactive components, comprising a component supplier having primary channels for supplying respective ones of said at least two reactive components to a component dispenser having secondary channels for separately discharging said at least two reactive components through orifices opening into a free target area at a distal tip end of the dispenser for external intimate mixing of the respective reactive components outside a distal tip end of said dispenser, wherein distributors are interposed between said primary and secondary channels for multiplying the number of each respective primary channel with at least a factor 2, adjacent ones of said orifices of said secondary channels being adjoined to said primary channels intended for supply of reactive components of different kind.

U.S. Pat. No. 7,018,357 "External mixer assembly" discloses a fluid delivery system for dispensing a multicomponent biological adhesive having at least a first component and a second component, the system comprising:
a housing configured to receive a plurality of reservoirs;
a discharge nozzle housing a conduit assembly having a plurality of conduits with a proximal end thereof in respective fluid communication with separate of said reservoirs, a distal end of said conduits defining at least two exit openings, wherein each of said plurality of reservoirs includes a sealable opening configured for being penetrated by a proximal end of a respective one of said plurality of conduits; and a deflector assembly provided on said housing, said deflector assembly having a deflector plate substantially parallel with said at least two exit openings, said deflector plate displaced at a distance from a distal-most end of said housing and oriented to deflect said first and second components after exiting from said at least two exit openings.

U.S. Pat. No. 8,616,468 "Spray applicator" discloses a spray assembly for dispensing a mixture, the assembly comprising: a connector configured for operable engagement with a first source of component and a second source of component; an elongated member operably connected to and extending distally from the connector, the elongated member including an inner shaft and an outer sleeve, and defining a vent lumen between the inner shaft and outer sleeve, the inner shaft defines at least a first lumen configured for fluid communication with the first source of component and a second lumen configured for fluid communication with the second source of component; a tip operably connected to the connector, the tip including an opening and defining a mixing chamber between a distal end of the elongated member and the opening of the tip; and an insert member configured to be received in the mixing chamber, the insert member defining at least one radially extending slot on a first end of the insert member and at least one radially extending slot on a second end of the insert member, each of the radially extending slots being configured to mix the first and second components prior to the combination exiting the opening in the tip.

There is a need in conveniently changing spray or drip tips to avoid procedure interruption if/when clogging of the tip occurs. Particularly in laparoscopic procedures, clogged tips may result in significant and undesirable delays in delivery of the sealant or hemostat.

SUMMARY OF THE INVENTION

Briefly, the present invention is directed to a device for mixing and expressing a multi-component sealant or hemostat or adhesive comprising at least two containers configured to contain and express two components into separate lumens of a multi-lumen cannula without mixing; an elongated expression tip having a main channel open at a proximal end with the cannula configured to slidably fit into the main channel; the tip containing a plurality of separate mixing chambers open at the distal end of the tip, each of the mixing chambers being in fluid communication with the main channel via an individual connecting channel at some position of the tip on the cannula; wherein the connecting channels openings into the main channel all having different distances from the distal end; wherein the tip is configured to slide on the cannula and advance distally when the main channel is pressurized.

In another aspect, the present invention is directed to a method of mixing and expressing a multi-component sealant or hemostat or adhesive comprising connecting at least two containers configured to contain and express two components to separate lumens of a multi-lumen cannula; connecting an elongated expression tip having a main channel open at a proximal end to the cannula, wherein the cannula is configured to slidably fit into the main channel; wherein the tip contains a plurality of separate mixing chambers open at the distal end of the tip, each of the mixing chambers being in fluid communication with the main channel via an individual connecting channel at some position of the tip on the cannula; wherein the connecting channels openings into the main channel all having different distances from the distal end; advancing the two components through separate lumens of the multi-lumen cannula without mixing to the tip, mixing the two components within a first mixing chamber and expressing the components through a first opening at the distal end of the tip; upon clogging of the first mixing chamber, continue advancing the two components through separate lumens of the multi-lumen cannula thus pressurizing the main channel; allowing the tip to slide on the cannula and advance distally thus opening a second mixing chamber to fluid communication with the main channel, mixing the two components within the second mixing chamber and expressing the components through a second opening at the distal end of the tip.

DETAILED DESCRIPTION OF THE INVENTION

Figure 1:
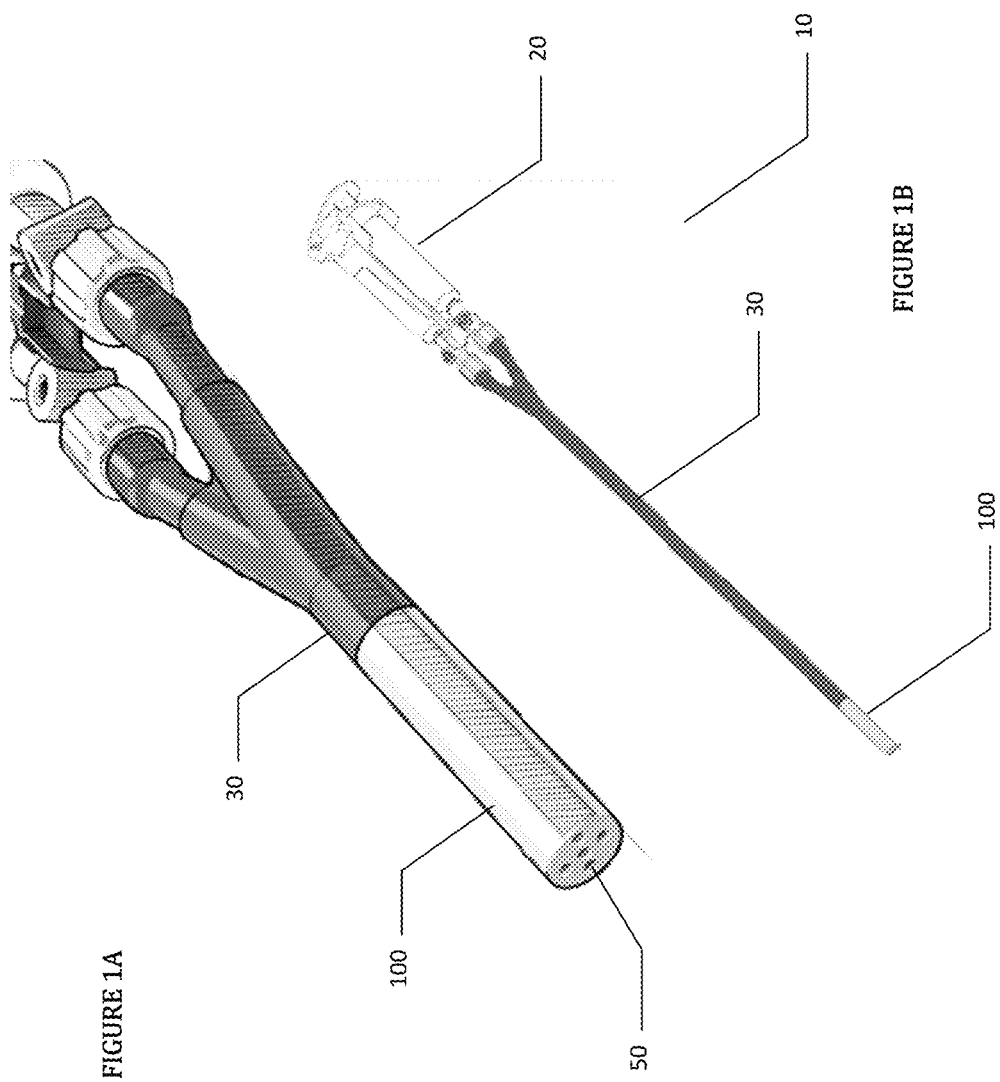
FIGS. 1A and 1B show perspective views of the inventive device for mixing and expressing multi-component compositions.

Referring now to FIG. 1B, an embodiment of a device 10 for mixing and expressing a multi-component sealant or hemostat or adhesive (or composition having one or more of these properties) is shown, comprising two or more containers or syringes 20 containing components of multi-part sealant or hemostat or adhesive, connected to a multi-lumen cannula 30 to which tip 100 having a plurality of exit ports 50 is attached.

Figure 2:
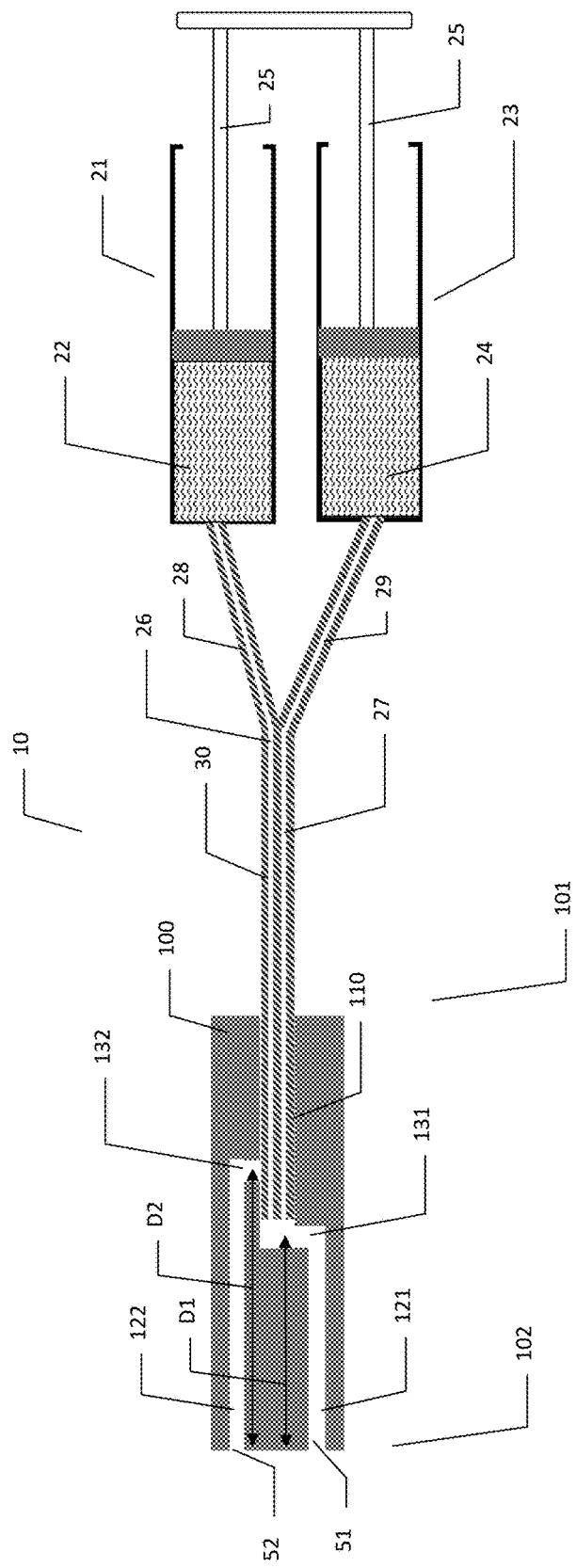
FIG. 2 shows a schematic cross-sectional view of the inventive device for mixing and expressing multi-component compositions.

Referring now to FIG. 2, an embodiment of device 10 is shown in more detail, with syringe 21 containing a first component 22 and syringe 23 containing a second component 24, syringes 21 and 23 having optionally interconnected plungers 25 for simultaneous expression of components 22 and 24. Syringes 21 and 23 are connected to multilumen cannula 30 via connectors 28 and 29, so that first component 22 and second component 24 can advance in multilumen cannula 30 towards tip 100 through lumens 26, 27 without mixing, thus preventing clogging of the multi-lumen cannula 30. In the shown embodiment, multilumen cannula 30 is a dual lumen cannula. Multilumen cannula 30 can have an additional lumen for gas (not shown) for gas-assisted spray.

Elongated tip 100 has a proximal end 101 that is closer to syringes 21 and 23 and an opposing distal end 102 relative to syringes 21 and 23. Ports 51, 52, from which the expression of the mixed liquid first component 22 and liquid second component 24 forming sealant or hemostat or adhesive are situated at distal end 102. Tip 100 has an axial main channel 110 open at proximal end 101 with cannula 30 configured to slidably fit into main channel 110 so that tip 100 is slidably moveable on cannula 30 and can advance distally when main channel 110 is pressurized due to clogging.

Tip 100 has a plurality (two are shown in the embodiment of FIG. 2) of separate mixing chambers 121, 122, open at distal end 102 of tip 100 to ports 51, 52 respectively. Each of mixing chambers 121, 122 are in fluid communication with main channel 110 via an individual connecting channel 131, 132 respectively. Connecting channels 131, 132 are open into main channel 110 at different distances from distal end 102, with distance of connecting channel 131 from distal end 102 D1 is indicated by arrow D1 and distance of connecting channel 132 from distal end 102 D2 is indicated by arrow D2. Distances D1 and D2 being different by at least the width of connecting channels 131, 132 and preferably by more than the width of connecting channels.

In some embodiments, lumens 26, 27 of multilumen cannula have inside diameter of 0.2-2 mm, such as 0.3 mm, 0.5 mm, 0.7 mm, 1 mm, 1.5 mm. Outside diameter of multilumen cannula 30 is 0.5-10 mm, such as is 1 mm, 1.5 mm, 2 mm, 3 mm, 5 mm, 7 mm, 10 mm. Inside diameter of main channel 110 corresponds to outside diameter of multilumen cannula 30, i.e. 0.5-10 mm, such as close to or slightly larger than 1 mm, 1.5 mm, 2 mm, 3 mm, 5 mm, 7 mm, 10 mm. Inside diameter of mixing chambers 121, 122 is 0.7-3 mm, such as 1 mm, 1.5 mm, 2 mm, 3 mm. Inside width of connecting channels 131, 132 is 0.3-3 mm, such as 0.5 mm, 0.7 mm, 1 mm, 1.5 mm, 2 mm. Distance D1 differs from distance D2 by more than width of connecting channels 131, 132 such as by 1.5-3 mm when diameter of connecting channels 131, 132 is 1 mm.

In some embodiments, two-part compositions comprise biological adhesive or sealant, forming fibrin glue, whereby first component 22 is fibrinogen and second component 24 is thrombin or thrombin analog or precursor. In other embodiments first component 22 is cross-linkable synthetic component, and second component 24 is a cross-linking agent.

Figure 3:
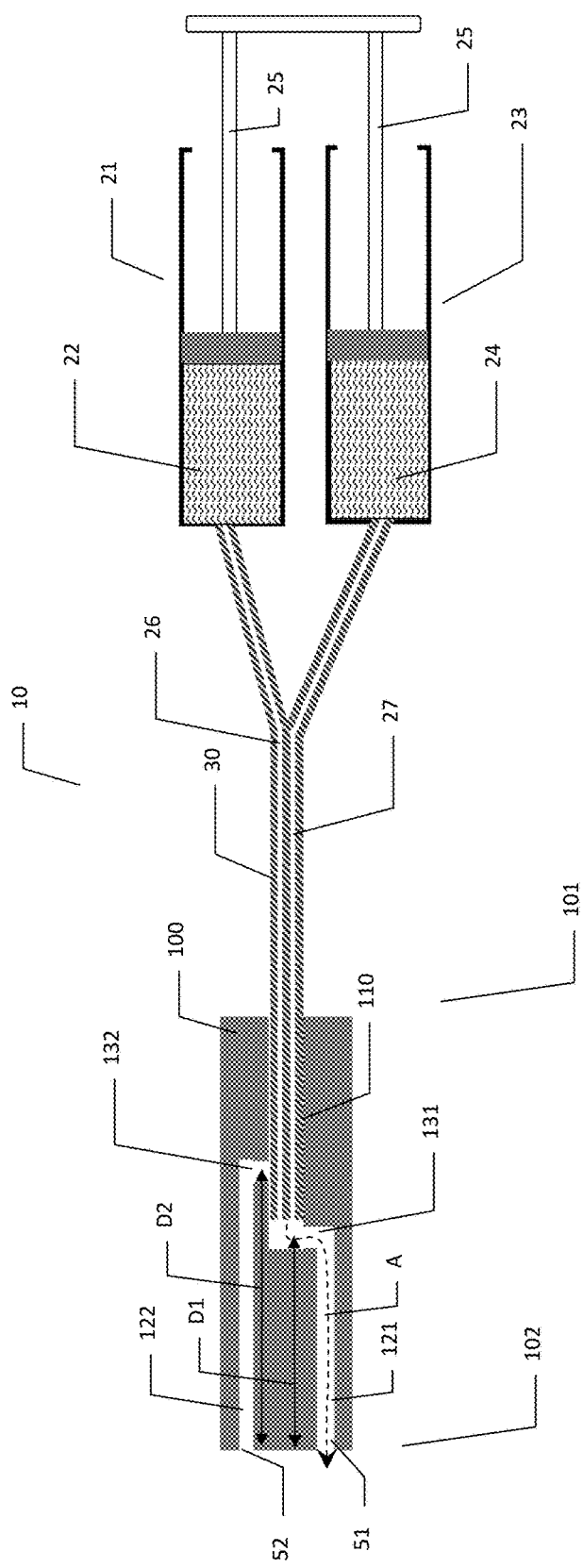
FIG. 3 shows a schematic cross-sectional view of the inventive device for mixing and expressing multi-component compositions.

Referring now to FIG. 3, in operation with connected plungers, depressing plungers 25 results in simultaneous advancing first component 22 and second component 24 through lumens 26 and 27 of multilumen cannula 30 towards tip 100 without mixing. First component 22 and second component 24 then enter connecting channel 131 and first mixing chamber 121, where first component 22 and second component 24 commingle and intermix to form a blend for sealant or hemostat or adhesive upon mixing. As shown by arrow A, the blend of first component 22 and second component 24 while undergoing additional mixing advance towards distal end 102 of tip 100 and exit tip 100 through port 51 toward targeted tissue, organ or wound (not shown). Exiting sealant or hemostat or adhesive formed through the blending and mixing of first component 22 and second component 24 can be expressed as a drip or as a spray, or combinations thereof.

Figure 4:
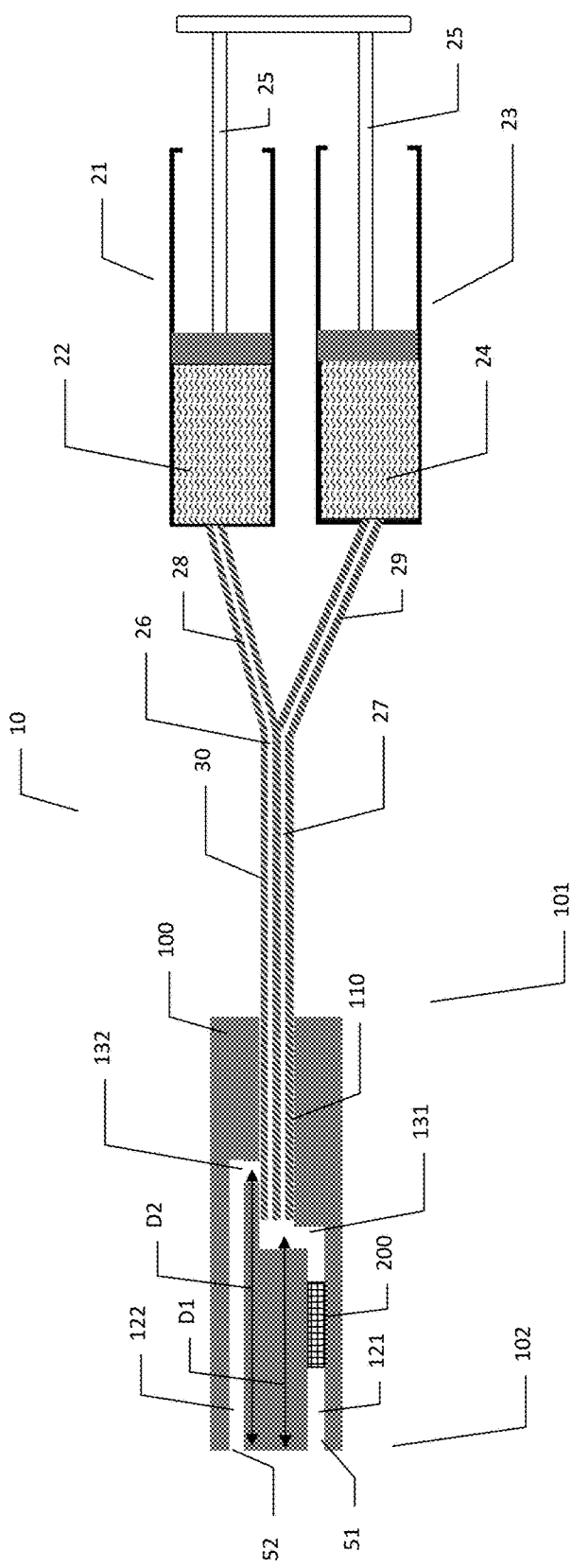
FIG. 4 shows a schematic cross-sectional view of the inventive device for mixing and expressing multi-component compositions.

The expression of sealant continues through port 51 as needed. Upon interruption of expression through port 51, due to operational activities such as performing another procedure, repositioning or retargeting device 10, etc., clogging connecting channel 131 and first mixing chamber 121 might occur due to gelling properties of the components. Such situation is shown in FIG. 4, with clog 200 forming in first mixing chamber 121. As a result of clog 200 blocking exit of the mixture of first component 22 and second component 24 from device 10 via port 51, upon health practitioner trying to restart expression and depressing plungers 25, pressure inside tip 100 increases. The pressure buildup is due to liquid components 22 and 24 having no path way for exiting tip 100 due to blockage by clog 200.

Figure 5:
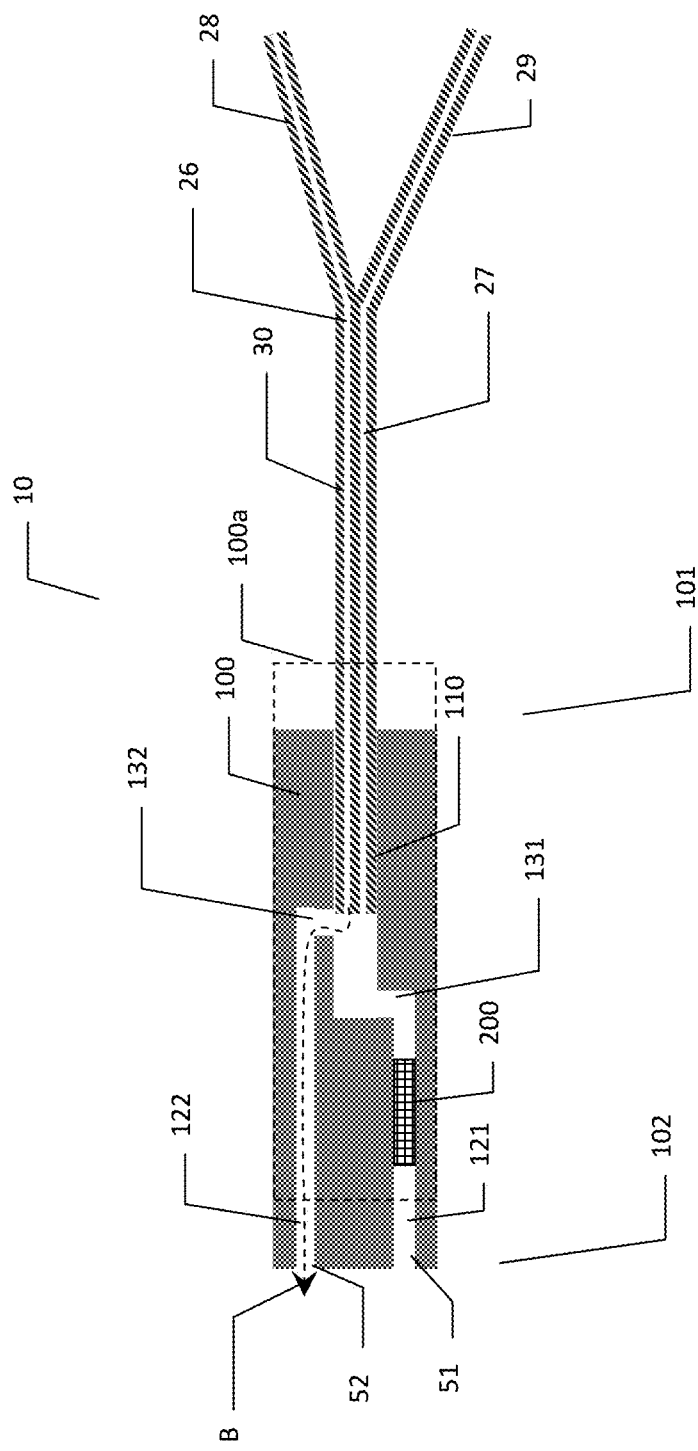
FIG. 5 shows a schematic cross-sectional view of a portion of the inventive device for mixing and expressing multi-component compositions.

Referring now to FIG. 5, where for simplification purposes, syringes 21 and 23 are not shown, increase in pressure results in sliding advancement of tip 100 distally, with tip 100 sliding on multilumen cannula 30 and opening a new portion of main channel 110 to the second connecting channel 132. The previous location of tip 100 corresponding to FIGS. 2-4, is schematically indicated by dashed box 100a. The distal advancement of tip 100 as shown in FIG. 5 opens a path for components 22 and 24 from main channel 110 through connecting channel 132 and into second mixing chamber 122.

As shown by arrow "B", despite clot 200, first component 22 and second component 24 can exit multilumen cannula 30 by advancing through connecting channel 132 and second mixing chamber 122 to commingle and intermix and form a blend for sealant or hemostat or adhesive. Mixed first component 22 and second component 24 while undergoing further mixing advance towards distal end 102 of tip 100 and exit tip 100 through second port 52 toward targeted tissue, organ or wound (not shown).

As shown above, clogging of a first connecting channel 131, and/or mixing chamber 121, and/or port 51 resulted in automatic change to second connecting channel 132, mixing chamber 122, and port 52. Advantageously, there is no need in manual tip 100 de-clogging, tip 100 replacement, or device 10 replacement during the treatment.

Embodiments described operate so as to switch to an unclogged mixing chamber automatically, meaning that the action occurred primarily as a result of internal pressure that caused a displacement and redirection of fluid flow. In another aspect, switching to an unclogged mixing chamber can be effected semi-automatically or manually. In semi-automatic operation, whereby practitioner manually advances and/or turns tip 100 to switch to second connecting channel 132, mixing chamber 122, and port 52.

Figure 6:
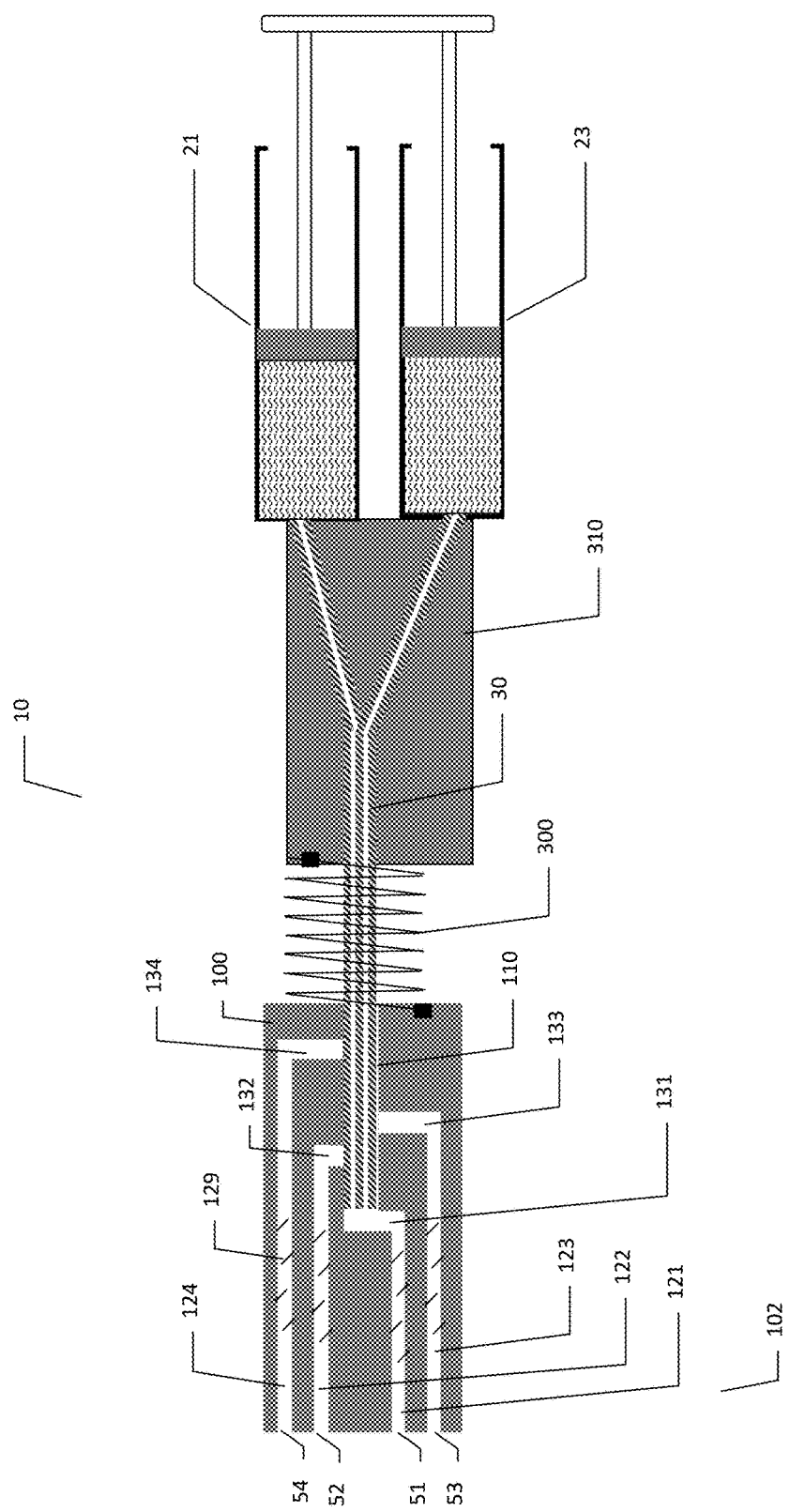
FIG. 6 shows a schematic cross-sectional view of the inventive device for mixing and expressing multi-component compositions.

Referring now to FIG. 6, an embodiment of device 10 similar to embodiments shown in FIGS. 2-5 is presented, with tip 100 having four connecting channels 131, 132, 133, 134, in fluid communication with corresponding mixing chambers 121, 122, 123, 124, terminating at distal end 102 in corresponding exit ports 51, 52, 53, 54. Similarly to embodiments shown in FIGS. 2-5, upon clogging of first mixing chamber 121 and/or corresponding connecting channel 131 and/or corresponding port 51, tip 100 automatically advances distally opening main channel 110 to second connecting channel 132 in fluid communication with corresponding mixing chamber 122, terminating at distal end 102 in corresponding exit port 52. Upon clogging of second mixing chamber 122 and/or corresponding connecting channel 132 and/or corresponding port 52, tip 100 further advances distally opening main channel 110 to third connecting channel 133 in fluid communication with corresponding mixing chamber 123, terminating at distal end 102 in corresponding exit port 53. Upon clogging of third mixing chamber 123 and/or corresponding connecting channel 133 and/or corresponding port 53, tip 100 further advances distally opening main channel 110 to fourth connecting channel 134 in fluid communication with corresponding mixing chamber 124, terminating at distal end 102 in corresponding exit port 54. While embodiment of FIG. 6 shows four mixing chambers and exit ports, any number of such components can be incorporated into tip 100, e.g. three to ten mixing chambers and exit ports, such as five.

Spring 300 connecting tip 100 to structure 310 affixed below syringes 21 and 23 provides resistance to tip 100 moving distally and controlling tip motion in distal direction. Elements 129 shown in mixing chambers 121-124 are optional static mixing elements or baffles facilitating inter-mixing of first component 22 and second component 24.

Figure 7:
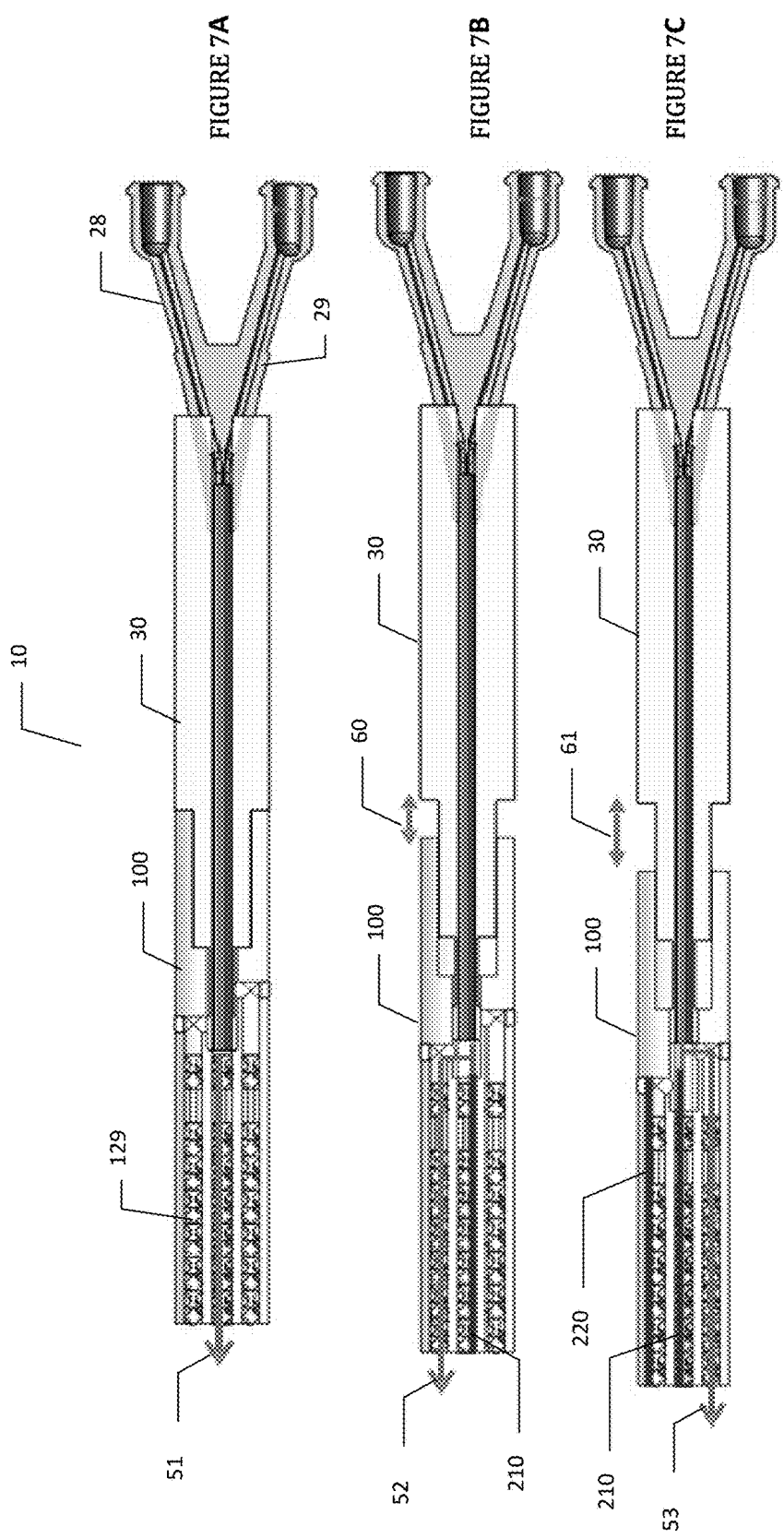
FIGS. 7A-C show schematic cross-sectional views of a portion of the inventive device for mixing and expressing multi-component compositions.

Referring now to FIGS. 7A-C, for simplification purposes, syringes 21 and 23 are not shown. In FIG. 7A, device 10 is shown with the expression proceeding through port 51. Upon formation of clog 210 as illustrated in FIG. 7B, tip 100 advances by distance 60 distally and expression continues through port 52. Upon formation of clog 220 as illustrated in FIG. 7C, tip 100 advances by distance 61 distally and expression continues through port 53.

Figure 8:
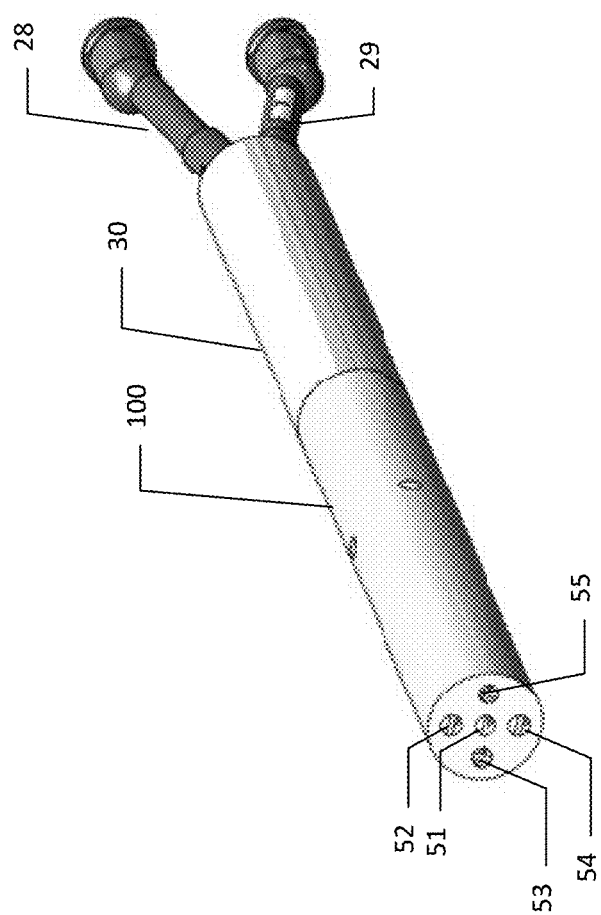
FIG. 8 shows a schematic perspective view of a portion of the inventive device for mixing and expressing multi-component compositions.

Referring now to FIG. 8, for simplification purposes, syringes 21 and 23 are not shown. Tip 100 is shown in a prospective view, mounted on multilumen cannula 30, with five ports 51, 52, 53, 54, 55 providing expression outlets from tip 100.

Figure 9:
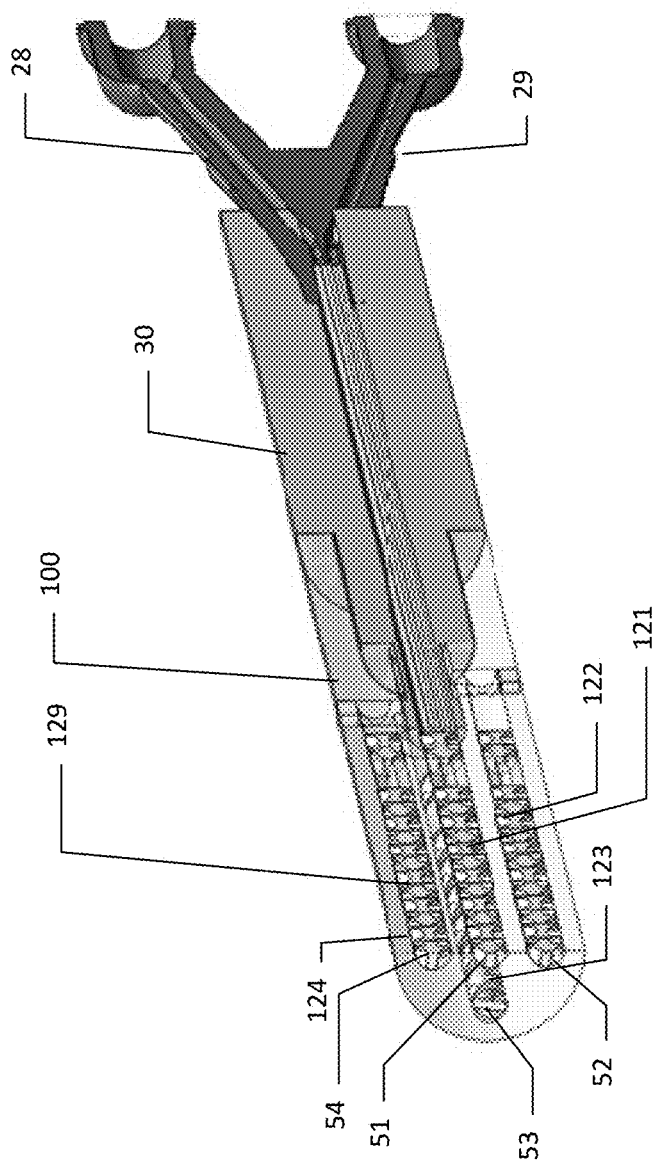
FIG. 9 shows a schematic perspective cross-sectional view of a portion of the inventive device for mixing and expressing multi-component compositions.

Referring now to FIG. 9, for simplification purposes, syringes 21 and 23 are not shown. Tip 100 is shown in a prospective cross-sectional view, mounted on multilumen cannula 30, with four ports 51, 52, 53, 54 visible and in fluid communication with four mixing chambers 121, 122, 123, 124 visible, having static mixers 129 in mixing chambers. Fifth mixing chamber and port are not visible in the cross-sectional view.

Figure 10:
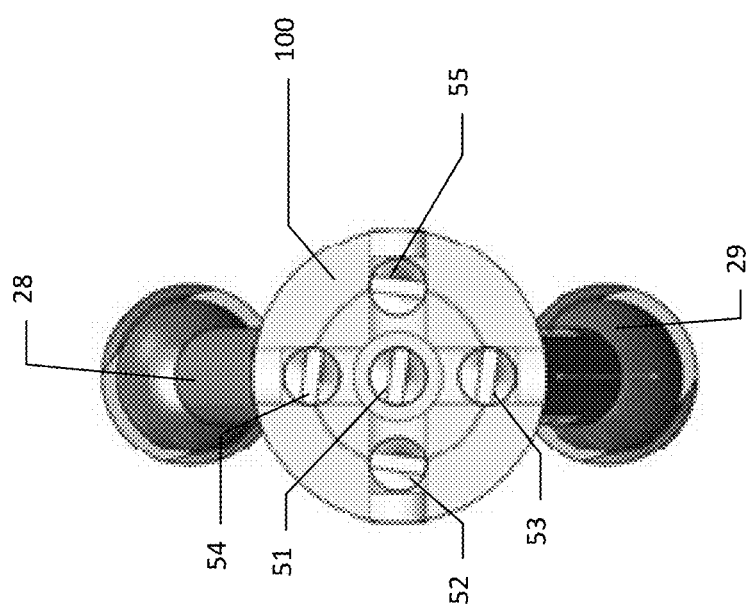
FIG. 10 shows a schematic frontal view of a portion of the inventive device for mixing and expressing multi-component compositions.

Referring now to FIG. 10, for simplification purposes, syringes 21 and 23 are not shown. Tip 100 is shown in a frontal view, with five ports 51, 52, 53, 54, 55 visible.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for delivering an at least partially mixed multi-component sealant or hemostat or adhesive formulation comprising:
   a) at least two containers of at least two separate, reactive components in fluid communication with at least two separate lumens of a multi-lumen cannula having outlets distal to the containers;
   b) an expression tip having a main channel that is open at a proximal end to the cannula and fitted over and beyond the cannula outlets;
      wherein the tip comprises a plurality of separate mixing chambers having outlets at the distal end of the tip and in fluid communication with the main channel via corresponding individual connecting channels, each individual connecting channel set at one of a plurality of distances relative to the distal end of the tip;
   wherein the tip moves distally when the main channel is pressurized due to an obstruction in at least one mixing chamber.

2. The device of claim 1, wherein said mixing chambers each terminate at the distal end of the tip with a spray port or an atomizing spray nozzle.

3. The device of claim 1, wherein said mixing chambers each terminate at the distal end of the tip with a drip port or a drip nozzle.

4. The device of claim 1, wherein said mixing chambers contain at least one of static mixing element and wherein at least some of said mixing chambers terminate at the distal end of the tip with a drip port or a drip nozzle wherein at least some of said mixing chambers terminate at the distal end of the tip with a spray port or an atomizing spray nozzle.

5. The device of claim 1, wherein a spring is attached to the tip that resists distal tip movement and wherein the tip is configured to be manually advanced distally or turned to switch to another mixing chamber.

6. The device of claim 1, wherein the main channel is pressurized due to a clog of at least partially reacted sealant.

7. The device of claim 1, wherein only upon the tip advancing distally, the connecting channel which is farther from the distal end of the tip begins to convey the multi-component sealant into its corresponding mixing chamber.

8. The device of claim 1, wherein prior to dispensing any reactive components, all but one of the connecting channels is blocked by the cannula and are not in fluid communication with the main channel.

9. The device of claim 1, wherein the multi-component sealant or hemostat or adhesive upon reaction comprises a fibrin glue, wherein the first component of the multi-component sealant comprises fibrinogen or fibrinogen analog, and wherein the second component of the multi-component sealant comprises an agent that converts fibrinogen to fibrin, preferably thrombin or thrombin precursor.

10. The device of claim 1, wherein the multi-component sealant or hemostat or adhesive upon reaction comprises a synthetic polymeric material, wherein the first component of the multi-component sealant comprises a cross-linkable compound, and the second component of the multi-component sealant comprises a cross-linking agent.

11. A method of mixing and expressing a multi-component sealant or hemostat or adhesive comprising
   a) connecting at least two containers configured to contain and express two components to separate lumens of a multi-lumen cannula;
   b) connecting an elongated expression tip having a main channel open at a proximal end to the cannula, wherein the cannula is configured to slidably fit into the main channel;
   wherein the tip contains a plurality of separate mixing chambers open at the distal end of the tip, each of the mixing chambers being in fluid communication with the main channel via an individual connecting channel at separate and distinct distances from the tip on the cannula;
   c) advancing the two components through separate lumens of the multi-lumen cannula without mixing to the tip;
   d) mixing the two components within a first mixing chamber; and
   e) expressing the components through a first opening at the distal end of the tip;
   f) upon clogging of the first mixing chamber, continuing to advance the two components through separate lumens of the multi-lumen cannula thus pressurizing the main channel;
   g) allowing the tip to slide on the cannula and advance distally to place a second mixing chamber in fluid communication with the main channel;
   h) mixing the two components within the second mixing chamber; and
   i) expressing the components through a second opening at the distal end of the tip.

12. The method of claim 11, wherein said mixing chambers each terminate at the distal end of the tip with a spray port or an atomizing spray nozzle.

13. The method of claim 11, wherein said mixing chambers each terminate at the distal end of the tip with a drip port or a drip nozzle.

14. The method of claim 11, wherein said mixing chambers contain at least one of static mixing element and wherein at least some of said mixing chambers terminate at the distal end of the tip with a drip port or a drip nozzle wherein at least some of said mixing chambers terminate at the distal end of the tip with a spray port or an atomizing spray nozzle.

15. The method of claim 11, wherein a spring is attached to the tip that resists distal tip movement and wherein the tip is configured to be manually advanced distally or turned to switch to another mixing chamber.

16. The method of claim 11, wherein the main channel is pressurized when the mixing chamber is clogged by an at least partially reacted multi-component sealant.

17. The method of claim 11, wherein upon the tip advancing distally, a second connecting channel that is farther from the distal end of the tip than the first connecting channel is in fluid communication with the multi-component sealant.

18. The method of claim 11, wherein prior to dispensing any components, all but one connecting channels are blocked by the cannula and are not in fluid communication with the main channel.

19. The method of claim 11, wherein the multi-component sealant or hemostat or adhesive upon reaction comprises a fibrin glue, wherein the first component of the multi-component sealant comprises fibrinogen or fibrinogen analog, and wherein the second component of the multi-component sealant comprises an agent that converts fibrinogen to fibrin, preferably thrombin of thrombin precursor.

20. The method of claim 11, wherein the multi-component sealant or hemostat or adhesive upon reaction comprises a synthetic polymeric material, wherein the first component of the multi-component sealant comprises a cross-linkable compound, and the second component of the multi-component sealant comprises a cross-linking agent.

* * * * *